United States Patent
Scates et al.

(10) Patent No.: US 6,303,813 B1
(45) Date of Patent: Oct. 16, 2001

(54) RHODIUM/INORGANIC IODIDE CATALYST SYSTEM FOR METHANOL CARBONYLATION PROCESS WITH IMPROVED IMPURITY PROFILE

(75) Inventors: Mark O. Scates, Friendswood; Valerie Santillan, Houston; Pramod Agrawal, Bay City; G. Paull Torrence; R. Jay Warner, both of Corpus Christi, all of TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/386,708

(22) Filed: Aug. 31, 1999

(51) Int. Cl.⁷ .................................................. C07C 51/12
(52) U.S. Cl. ........................ 562/519; 562/517; 562/607
(58) Field of Search .................... 562/519, 607, 562/517

(56) References Cited

U.S. PATENT DOCUMENTS

| | | | |
|---|---|---|---|
| 3,769,329 | 10/1973 | Paulik et al. | 260/488 |
| 4,994,608 | 2/1991 | Torrence et al. | 562/519 |
| 5,001,259 | 3/1991 | Smith et al. | 562/519 |
| 5,026,908 | 6/1991 | Smith et al. | 562/519 |
| 5,144,068 | 9/1992 | Smith et al. | 562/519 |
| 5,625,095 | 4/1997 | Miura et al. | 562/519 |

FOREIGN PATENT DOCUMENTS

WO 98/17619   4/1998   (WO) .............................. C07C/51/00

OTHER PUBLICATIONS

Watson, The Cativa Process for the Production of Acetic Acid Chem. Ind. (Dekker) (1998) 75 Catalysis of Organic Reactions, pp 369–380.

Primary Examiner—Paul J. Killos
Assistant Examiner—Robert W. Deemie
(74) Attorney, Agent, or Firm—M. Susan Spiering

(57) ABSTRACT

The method of the present invention provides an improvement upon prior art methanol carbonylation methods which substantially reduces the production of carbonyl impurities.

The production of carbonyl impurities, particularly acetaldehyde, crotonaldehyde, and 2-ethyl crotonaldehyde, in methanol carbonylation reactions has been found to decrease by maintaining a partial pressure of hydrogen between about 0.1 and 4 psia at reaction total pressure of from about 15 to about 40 atmospheres total reaction pressure.

18 Claims, No Drawings

RHODIUM/INORGANIC IODIDE CATALYST SYSTEM FOR METHANOL CARBONYLATION PROCESS WITH IMPROVED IMPURITY PROFILE

BACKGROUND OF THE INVENTION

1. Field of the Invention

The present invention is directed to an improvement in the process for the carbonylation of methanol to produce acetic acid. More specifically, the improved method of the present invention reduces the formation of carbonyl impurities in the carbonylation reaction by way of conducting the reaction with relatively low hydrogen partial pressures in the reactor.

2. The Related Art

Among currently employed processes for synthesizing acetic acid one of the most useful commercially is the catalyzed carbonylation of methanol with carbon monoxide as taught in U.S. Pat. No. 3,769,329 issued to Paulik et al. on Oct. 30, 1973. The carbonylation catalyst comprises rhodium, either dissolved or otherwise dispersed in a liquid reaction medium or else supported on an inert solid, along with a halogen-containing catalyst promoter as exemplified by methyl iodide. Generally, the reaction is conducted with the catalyst being dissolved in a liquid reaction medium through which carbon monoxide gas is continuously bubbled. Paulik et al. disclose that water may be added to the reaction mixture to exert a beneficial effect upon the reaction rate, and water concentrations between about 14–15 wt % are typically used. This is the so-called "high water" carbonylation process.

An alternative to the "high water" carbonylation process is the "low water" carbonylation process, as described in U.S. Pat. Nos. 5,001,259, 5,026,908, and 5,144,068. Water concentrations below 14 wt % and even below 10 wt % can be used in the "low water" carbonylation process. Employing a low water concentration simplifies downstream processing of the desired carboxylic acid to its glacial form.

One improvement which has been made to the "low water" carbonylation process is disclosed in U.S. Pat. No. 4,994,608, which discloses a carbonylation process utilizing a rhodium catalyst wherein a partial pressure of hydrogen between 4 and 150 psia is maintained in the carbonylation reactor. The presence of the hydrogen is disclosed as having the effect of increasing the rate of carbonylation by keeping the rhodium in its active rhodium (I) form. It is noted in the '608 patent that it is possible to operate a methanol carbonylation process at relatively low levels of hydrogen partial pressure, albeit at relatively low levels of rhodium. See FIG. 1, as well as Table II, col. 14, lines 8 through 32 of the '608 patent.

In the present invention, however, it has been found that while the presence of hydrogen in the carbonylation reaction does in fact increase the carbonylation rate, the rate of formation of undesirable by-products, such as crotonaldehyde, 2-ethyl crotonaldehyde, butyl acetate, and hexyl iodide, also increases. Since hydrogen can often be an impurity in carbon monoxide feedstocks used in methanol carbonylation, the partial pressure of hydrogen should be maintained such that the rate of formation of by-products is limited. It is therefore an object of the present invention to provide a "low water" carbonylation process wherein a partial pressure of hydrogen in the carbonylation reaction is maintained at a level which limits the rate of by-product formation.

It is postulated in an article by Watson, The Cativa™ Process for the Production of Acetic Acid, Chem. Ind. (Dekker) (1998) 75 Catalysis of Organic Reactions, pp. 369–380 that enhanced rhodium catalyzed systems have increased standing levels of rhodium-acyl species which will form free acetaldehydes at a higher rate. The higher rate of acetaldehyde formation can lend to the increased production of permanganate reducing compounds.

The precise chemical pathway within the methanol carbonylation process that leads to the production of crotonaldehyde, 2-ethyl crotonaldehyde and other permanganate reducing compounds is not well understood. One prominent theory for the formation of the crotonaldehyde and 2-ethyl crotonaldehyde impurities in the methanol carbonylation process is that they result from aldol and cross-aldol condensation reactions starting with acetaldehyde. Substantial efforts have been directed to removing acetaldehyde.

Conventional techniques used to remove acetaldehyde and carbonyl impurities have included treatment of acetic acid with oxidizers, ozone, water, methanol, amines, and the like. In addition, each of these techniques may or may not be combined with the distillation of the acetic acid. The most typical purification treatment involves a series of distillations of the product acetic acid. Likewise, it is known to remove carbonyl impurities from organic streams by treating the organic streams with an amine compound such as hydroxyl amine which reacts with the carbonyl compounds to form oximes followed by distillation to separate the purified organic product from the oxime reaction products. However, this method of treating the product acetic acid adds cost to the process.

There is disclosed in U.S. Pat. No. 5,625,095 to Miura et al. and PCT International Application No. PCT/US97/18711, Publication No. WO 98/17619 various methods of removing acetaldehydes and other impurities from a rhodium-catalyzed acetic acid production process. Generally, these methods involve extracting undesirable impurities from process streams to reduce acetaldehyde concentrations in the system.

These processes have achieved a certain level of success in controlling carbonyl impurity concentrations within product acetic acid produced by methanol carbonylation. Nonetheless, even with the use of these prior art removal methods, acetaldehyde and carbonyl impurities that derive from acetaldehyde, particularly, crotonaldehyde and 2-ethyl crotonaldehyde, continue to be a problem in product acetic acid produced by methanol carbonylation. Accordingly, a need remains for a method to control carbonyl impurities in product acetic acid produced by methanol carbonylation, particularly one which can be performed economically without adding to the impurities in the product acetic acid or incorporating additional processing steps. It has been found that reduced levels of hydrogen lead to improved purity profiles.

SUMMARY OF THE INVENTION

There is provided in the present invention an improved process for producing acetic acid by reacting methanol with a carbon monoxide feedstock in a carbonylation reactor holding a reaction medium containing a catalytically effective amount of rhodium which includes maintaining catalyst stability and system productivity by maintaining in said reaction medium during the course of said reaction at least a finite concentration (0.1 wt %) up to less than 14 wt % of water together with (a) a salt soluble in the reaction medium at the reaction temperature in an amount operative to maintain a concentration of ionic iodide in the range of from about 2 to about 20 wt % effective as a catalyst stabilizer and co-promoter, (b) from about 1 to 20 wt % methyl iodide, (c) from about 0.5 to 30 wt % methyl acetate, (d) a partial pressure of hydrogen between about 0.1 and 4 psia at reaction conditions comprising 15 to 40 atmospheres total reaction pressure (absolute), (e) a rhodium concentration of at least 500 ppm by weight based on the weight of rhodium metal in the reaction mixture; and (f) acetic acid. Typically, a hydrogen partial pressure is maintained between about 1 and 4 psia, and sometimes between about 1.5 and 3.5 psia.

The improvement may be practiced wherein said hydrogen partial pressure is maintained by venting or purging gaseous components of the reaction medium. The invention is also embodied where the ratio of hydrogen to carbon monoxide fed to said carbonylation reactor is from 0 mole percent to about 0.5 mole percent, although a concentration of hydrogen in the carbon monoxide fed to the carbonylation reactor from about 0.001 mole percent to about 0.3 mole percent is more typical. A concentration of hydrogen in the carbon monoxide fed to said carbonylation reactor is from about 0.005 mole percent to about 0.0250 mole percent may likewise be employed. It will be appreciated by those of skill in the art that the hydrogen may be fed to the reactor with the carbon monoxide feed, or, hydrogen may be generated in situ by way of the water gas shift reaction. The source of the hydrogen present in the reactor is unimportant, so long as the requisite partial pressure is maintained.

The improved process is advantageously practiced wherein the concentration of rhodium in the reaction medium is maintained between about 500 and 5000 parts per million rhodium by weight. A rhodium concentration in the reaction medium within a range of from about 600 to about 2000 parts per million rhodium by weight is more typical; whereas a range of from about 750 to about 1500 parts per million by weight rhodium is still more preferred.

The catalyst stabilizer is selected from the group consisting of salts which are soluble in the reaction mixture. Specific stabilizers include lithium iodide, lithium acetate as well as salts of sodium, potassium, phosphorous, nitrogen and the like. A comprehensive but non-exhaustive list appears in Table V of U.S. Pat. No. 5,026,98 to Smith et al., the disclosure of which is hereby incorporated by reference. It will be recognized that it is the concentration of iodide ion in this catalyst system which is important, and not the cation associated with the iodide. Further, at a given molar concentration of the iodide anion, the nature of the cation is not as significant as the effect of the iodide concentration. Any metal salt, or any salt of any organic cation can be used provided the salt is sufficiently soluble in the reaction medium to provide the desired level of iodide. Also, the ionic iodide stabilizer/co-promoter may be in the form of a soluble salt of an alkali metal or an alkaline earth metal salt or a quaternary ammonium or phosphonium salt that will generate an effective amount of iodide ion in the reaction solution. Iodide or acetate salts of lithium, sodium and potassium are particularly useful.

The concentration of water in the reactor is generally maintained at from about 0.1 wt % to about 14 wt %, whereas the partial pressure of hydrogen is maintained between about 1 and about 4 psia, and more preferably the partial pressure of hydrogen is maintained between about 1.5 and about 3.5 psia.

A particularly preferred process includes producing acetic acid by reacting methanol with carbon monoxide in a carbonylation reactor holding a reaction medium containing a homogeneous rhodium catalyst, while maintaining catalyst stability and system productivity by maintaining in the reaction medium during the course of the reaction from about 1 to about 10 wt % of water together with (a) a salt soluble in the reaction medium at the reaction temperature in an amount operative to maintain a concentration of ionic iodide in the range of from about 2 to about 20 wt % effective as a catalyst stabilizer and co-promoter, (b) from about 1 to 20 wt % methyl iodide, (c) from about 0.5 to 30 wt % methyl acetate, (d) a partial pressure of hydrogen between about 0.1 and 4 psia at reaction conditions comprising 15 to 40 atmospheres total reaction pressure, (e) a rhodium concentration of at least about 500 ppm rhodium by weight based on the weight of rhodium metal, and (f) acetic acid.

DESCRIPTION OF SPECIFIC EMBODIMENTS

The invention is described in detail below in connection with examples which are provided for purposes of illustration only. The examples in no way limit the spirit and scope of the present invention which is set forth in the appended claims.

It will be appreciated that the rhodium catalyzed process for preparing acetic acid is well known. Thus, the invention will be described in terms of differences from prior art processes such as are described in U.S. Pat. Nos. 5,001,259; 5,026,908; and 5,144,068, the disclosures of which are incorporated herein by reference.

There are two criteria which are desirably satisfied to maintain optimal performance of a reaction system for the rhodium-catalyst carbonylation of methanol to acetic acid. This is over and above the maintenance of a stable catalyst system from which the rhodium catalyst does not precipitate during the course of product recovery. First, it is desired to maintain a high productivity in the carbonylation reactor itself, as measured by the quantity of acetic acid formed per unit time per unit volume or weight of liquid reaction medium contained in the reactor. This might be termed "reactor productivity" or "reactor space-time yield", also referred to as "STY".

Second, the present process improvement contemplates the maintenance of optimal productivity, as measured by the ultimately-recovered glacial acetic acid in the combined system including both the carbonylation reactor and the product recovery system. It will be recognized by anyone skilled in the art that water is an undesirable component of the crude acetic acid and that the more water there is in this stream the greater will be the operating costs and required capital investment in the product recovery-purification system. Thus, there is also a "system productivity" to be considered in addition to the "reaction productivity", with the "system productivity" depending upon the degree to which water is kept out of the residue of the crude product stream. The dryer this stream is, the higher will be the over-all system productivity so long as reaction productivity is maintained.

For the purposes of this invention, the catalyst which is employed includes a rhodium component and a halogen promoter in which the halogen is either bromine or iodine. The catalyst system is preferably generally homogeneous as is well known. The rhodium component of the catalyst system of the present invention is believed to be present in the form of a coordination compound of rhodium with a halogen component providing at least one of the ligands of such coordination compound. In addition to the coordination of rhodium and halogen, it is also believed that carbon monoxide ligands form coordination compounds or complexes with rhodium.

The rhodium component of the catalyst system in the present invention may be provided by introducing into the reaction zone rhodium in the form of rhodium metal, rhodium salts and oxides, organic rhodium compounds, coordination compounds of rhodium and the like.

The halogen promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol which is carbonylated. For example, in the carbonylation of methanol to acetic acid, the halide promoter will comprise methyl halide, and more preferably methyl iodide.

The reaction medium employed may include any solvent compatible with the catalyst system and may include pure alcohols, or mixtures of the alcohol feedstock and/or the desired carboxylic acid and/or esters of these two compounds. The preferred solvent and reaction medium for the process of this invention comprises the carboxylic acid product. Thus, in the carbonylation of methanol to acetic acid, the preferred solvent is acetic acid.

Water is also added to the reaction medium, but at relatively low concentrations; that is, concentrations below about 14 wt %. It has been shown (U.S. Pat. Nos. 5,001,259, 5,026,908, and 5,144,068) that reaction rates substantially equal to and above reaction rates obtained with water concentrations above about 14 wt % can be achieved with water concentrations below 14 wt % and as low as 0.1 wt %. In accordance with the present invention, the desired reaction rates are obtained even at low water concentrations by including in the reaction medium an ester which corresponds to the alcohol being carbonylated and the acid product of the carbonylation reaction and, most preferably, an additional iodide ion which is over and above the iodide which is present as a catalyst promoter such as methyl iodide or other organic iodide. Thus, in the carbonylation of methanol to acetic acid, the ester is methyl acetate and the additional iodide co-promoter is an iodide salt, with lithium iodide being preferred.

It has been found that under low water concentrations, methyl acetate and iodide ion act as rate promoters only when relatively high concentrations of each of these components are present and that the promotion is higher when both of these components are present simultaneously, as disclosed in U.S. Pat. Nos. 5,001,259, 5,026,908, and 5,144,068.

Additionally, it has been shown that in reaction mediums having a methyl acetate concentration of greater than about 2 wt %, iodide ion is necessary not only to increase the reaction rate but also to stabilize the rhodium catalyst due to the deleterious effect of high methyl acetate concentrations on its stability, even at high water concentrations.

Table I gives suitable ranges of some of the various reaction components used in a process of the present invention.

TABLE I

Broad and preferred ranges of Components.

| | STABILIZATION | | RATE ENHANCEMENT | |
| --- | --- | --- | --- | --- |
| | Broad wt % | Preferred wt % | Broad wt % | Preferred wt % |
| Water | 0.1–14 | 1–10 | 0.1–14 | 1–10 |
| Inorganic Iodide (As Lithium iodide) | 2–20 | 5–15 | 2–20 | 10–20 |
| Methyl Acetate | 0.5–30 | 0.5–5 | 0.5–30 | 2–5 |
| Methyl iodide | 1–20 | 5–16 | 1–20 | 5–16 |
| Acetic Acid | balance | balance | balance | balance |
| Rhodium (ppm) | 500–5000 | 750–1500 | 500–5000 | 750–1500 |

Amounts of water, iodide ion, methyl acetate, and methyl iodide are set forth as both a broad range and a preferred, or optimal, range, for obtaining both catalyst stabilization and reaction rate enhancement. The "preferred" range is that which is preferred from the standpoint of optimal performance of the entire system including the primary product recovery system as explained hereinabove. It will be seen that the recommended concentrations are the same for both stabilization and also rate enhancement with one exception. The exception is that the "preferred" range for methyl acetate is 0.5–5 wt % for catalyst stabilization whereas it is 2–5 wt % for optimal rate enhancement. Broadly of course, this means that in either case a range between 0.5 wt % and 5 wt % would be satisfactory, but that, depending upon whether it is catalyst stabilization or maximal rate enhancement that one aims to maximize in a given plant operating situation, the bottom end of the desired methyl acetate range is slightly higher when maximal rate enhancement is being sought. Additionally, the amount of rhodium added to the system can be increased as the hydrogen partial pressure in the carbonylation reactor is decreased, since the decreased hydrogen can lead to a loss of catalyst activity.

An important addition to the reaction medium and the subject matter of the present invention is a finite concentration of hydrogen. As shown in U.S. Pat. No. 4,994,608, in a carbonylation process wherein the water content is below about 14 wt %, hydrogen in the reactor is not merely an inert gas, but actually improves the reaction rate for the production of carboxylic acid. However, it has now been found that a high partial pressure of hydrogen in the carbonylation reactor will also increase the formation of by-products, such as crotonaldehyde, 2-ethyl crotonaldehyde, butyl acetate and hexyl iodide, beyond desired levels. To achieve the improved carbonylation reaction rates for the formation of the desired carboxylic acid and limit the rate of by-product formation, the carbonylation reactor should contain a hydrogen partial pressure of between about 0.1 and 4 psia at the reactor conditions of 150–250° C. and 15 to 40 atmospheres total reaction pressure. Preferably, the hydrogen partial pressure will be between about 1 and 4 psi, and more preferably between about 1.5 and 3.5 psia. All pressures as herein stated refer to absolute pressure.

One source of hydrogen in the carbonylation reactor is from the production of hydrogen by reaction in the reaction medium, such as by the water gas shift reaction. Hydrogen can also be added in the carbon monoxide feed to provide the necessary hydrogen to the carbonylation reactor. The hydrogen in the carbon monoxide feed can be added deliberately, suitably in a feed concentration of hydrogen of between about 0 mol % and 0.3 mol % preferably between about 0 mol % and 0.0250 mol %. Typically, however, most carbon monoxide feedstocks contain hydrogen as an impurity in an amount between about 0.001 mol % and 0.5 mol %. In such a case, when hydrogen is an impurity in the carbon monoxide feedstock, no hydrogen need be added to the carbon monoxide feed. The source of the hydrogen present in the reactor is unimportant, so long as the requisite partial pressure is maintained.

It will be appreciated that the hydrogen partial pressure can be controlled and manipulated by appropriate control of the reactor vent or purge. In cases where the hydrogen content of the feed is very low and most of the hydrogen is produced in situ, the amount of hydrogen which must be vented or purged is minimal while in other cases it is desirable to remove hydrogen in order to maintain the hydrogen partial pressure within the desired range.

With the successes of previous improvements to the chemistry of the carbonylation reaction, particularly the reduction of the water concentration maintained during the reaction, we have learned that as the water concentration decreases, carbonyl impurities, namely acetaldehyde and carbonyl impurities that derive from acetaldehyde, particularly, crotonaldehyde and 2-ethyl crotonaldehyde, increase dramatically. Despite there being no definitively recognized chemical pathway within the carbonylation reaction which leads to the formation of acetaldehyde, crotonaldehyde, and 2-ethyl crotonaldehyde, we have learned that the formation of these impurities is a multifaceted problem. Indeed, other factors may also affect their production.

Nonetheless, we have discovered that by maintaining the hydrogen partial pressures at or below levels previously recognized as beneficial, particularly at low water concentrations, the production of acetaldehyde and its derivatives, particularly crotonaldehyde and 2-ethyl crotonaldehyde, is dramatically reduced. Previously in the prior art, hydrogen partial pressure has been maintained in the reactor concentrations at about or greater than 4 psia. By maintaining the hydrogen partial pressure during the carbonylation reaction at about 4 psia or less, quite unexpectedly, we have found the production of crotonaldehyde, and 2-ethyl crotonaldehyde, to be substantially reduced.

In accordance with the present invention, the carbonylation reaction may be carried out by intimately contacting methanol, which is in the liquid phase, with gaseous carbon monoxide bubbled through a liquid reaction medium containing the rhodium catalyst, halogen-containing promoting component, alkyl ester, and additional soluble iodide salt promoter, at conditions of temperature and pressure suitable to form the carbonylation product. Thus, if the feed is methanol, the halogen-containing promoting component will comprise methyl iodide, the alkyl ester will comprise methyl acetate and if an iodide salt is employed, the iodide ion will comprise any of numerous soluble salts which are useful. When an iodide stabilizer is used, it will be recognized that it is the concentration of iodide ion in this catalyst system that is important and not the cation associated with the iodide, and that at a given molar concentration of iodide the nature of the cation is not as significant as the effect of the iodide concentration. Any metal salt, or any salt of any organic cation, can be used provided that the salt is sufficiently soluble in the reaction medium to provide the desired level of the iodide. The salt can be a quaternary salt of an organic cation or the salt of an inorganic cation, preferably it is an iodide salt of a member of the group consisting of the metals of Group Ia and Group IIa of the periodic table as set forth in the "*Handbook of Chemistry and Physics*" published by CRC Press, Cleveland, Ohio 1975–76 (56th edition). In particular, alkali metal iodides are useful, with lithium iodide being most preferred.

The reaction temperature will be approximately 150–250° C., with the temperature range of about 180–220° C. being the preferred range. The carbon monoxide partial pressure in the reactor can vary widely but is typically about 2–30 atmospheres, and preferably, about 4–15 atmospheres. Because of the partial pressure of by-products and the vapor pressure of the contained liquids, the total reactor pressure will range from about 15 to 40 atmospheres.

A reaction system which is employed, wherein the present improvement is used, comprises (a) a liquid-phase homogeneous carbonylation reactor, (b) a so-called "flasher", and (c) a "methyl iodide-acetic acid splitter column". The carbonylation reactor is typically a stirred autoclave within which the reacting liquid contents are maintained automatically at a constant level. Into this reactor there are continuously introduced fresh methanol, sufficient water to maintain at least a finite concentration of water in the reaction medium, recycled catalyst solution from the flasher base, and recycled methyl iodide and methyl acetate from the overhead of the methyl iodide-acetic acid splitter column. Alternate distillation systems can be employed so long as they provide means for recovering the crude acetic acid and recycling to the reactor catalyst solution, methyl iodide, and methyl acetate. In the preferred process, a mixed carbon monoxide/hydrogen feed is continuously introduced into the carbonylation reactor just below the agitator which is used to stir the contents. The mixed gaseous feed is, of course, thoroughly dispersed through the reacting liquid by this means. A gaseous purge stream is vented from the reactor to prevent buildup of gaseous by-products and to maintain a set carbon monoxide partial pressure at a given total reactor pressure. By controlling the venting of gases, it is also possible to control the hydrogen partial pressure in the reactor. The temperature of the reactor is controlled automatically, and the carbon monoxide/hydrogen feed is introduced at a rate sufficient to maintain the desired total reactor pressure.

Liquid product is drawn off from the carbonylation reactor at a rate sufficient to maintain a constant level therein and is introduced to the flasher at a point intermediate between the top and bottom thereof. In the flasher the catalyst solution is withdrawn as a base stream (predominantly acetic acid containing the rhodium and the iodide salt along with lesser quantities of methyl acetate, methyl iodide, and water), while the overhead of the flasher comprises largely the product acetic acid along with methyl iodide, methyl acetate, and water. A portion of the carbon monoxide and hydrogen along with gaseous by-products such as methane, hydrogen, and carbon dioxide exits the top of the flasher.

The product acetic acid drawn from the base of the methyl iodide-acetic acid splitter column (it can also be withdrawn as a side stream near the base) is then drawn off for final purification as desired by methods well known in the art and which are outside the scope of the present invention. The overhead from the methyl iodide-acetic acid splitter, comprising mainly methyl iodide and methyl acetate, is recycled to the carbonylation reactor.

The primary reaction control method comprises continually analyzing the liquid contents of the reactor as well as the carbon monoxide and hydrogen content of the gas in the reactor vent and, on the basis of these analyses, controlling the flow of carbon monoxide, hydrogen, water, methanol, and methyl iodide to maintain the specified reaction medium composition. It should be further explained that the methanol addition to the carbonylation reactor is based not on an analysis of its contents for methanol but, rather, on analysis for methyl acetate content. Most of the methanol is converted almost immediately to methyl acetate when it enters the carbonylation reactor.

In a continuous process which is described above, the catalyst system is maintained, with the reactants being continuously supplied to the reaction zone containing the catalyst system at the desired temperature and pressure. The products are continuously withdrawn, as described above by withdrawing a portion of the solution containing the catalyst system, unreacted feed, equilibrium components, and the desired product. The desired product is then separated from such solution to permit recycling of the catalyst containing solution which includes unreacted feed and also equilibrium components.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES 1–4

A continuous pilot plant equipped generally as described above with a 4-liter reactor operating at 1.5 liter reaction volume was used to investigate the effect of hydrogen partial pressure ($H_2PP$) on the formation of by-products while carbonylating methanol. Operating conditions and results appear in Table II below. "Column Residue Impurities" refers to impurities in the crude acetic acid product and "$H_2PP$" refers to the partial pressure of hydrogen in the reaction vessel in pounds per square inch absolute.

TABLE II

| Hydrogen Partial Pressure Data | | | | |
| --- | --- | --- | --- | --- |
| EXAMPLES | 1 | 2 | 3 | 4 |
| Reactor $H_2pp$ (psia) | 2.0 | 3.3 | 9.4 | 14.6 |
| Methanol Feed (grams/min) | 14.9 | 15.0 | 15.0 | 15.0 |
| Reactor Composition | | | | |
| Methyl Iodide, wt % | 10.6 | 11.0 | 10.8 | 10.9 |
| Methyl Acetate, wt % | 2.6 | 2.5 | 2.5 | 2.5 |
| Water, wt % | 4.0 | 4.0 | 4.1 | 4.3 |
| Rh, ppm | 631 | 652 | 657 | 651 |
| LiI, wt % | 6.6 | 8.2 | 8.4 | 8.7 |
| Rx. Temp. deg C. | 195.2 | 194.0 | 191.8 | 192.3 |
| Column Residue Impurities | | | | |
| Propionic Acid, ppm | 140 | 197 | 363 | 500 |
| Crotonaldehyde, ppm | 1 | 4 | 6 | 8 |
| 2-ethyl-Crotonaldehyde, ppm | 1 | 3 | 6 | 8 |
| Butyl Acetate, ppm | 3 | 6 | 13 | 16 |

As can be seen in Table II the column residue impurity profile is improved at lower hydrogen partial pressures in the reactor.

While the foregoing examples demonstrate the reduction of crotonaldehyde and the like, it will be appreciated by one of skill in the art that other impurities and byproducts in rhodium catalyzed carbonylation systems include, butyl acetate, butyl iodide, ethyl acetate, ethyl iodide, hexyl iodide and high boiling impurities. The present invention appears to minimize production of these impurities as well.

While the invention has been described in detail, various modifications of particular embodiments within the spirit and scope of the present invention will be readily apparent to those of skill in the art. The invention is defined in the appended claims.

What is claimed is:

1. In a process for producing acetic acid by reacting methanol with a carbon monoxide feedstock in a carbonylation reactor holding a reaction medium containing a catalytically effective amount of rhodium, the improvement to reduce impurities which comprises:

maintaining catalyst stability and system productivity by maintaining in said reaction medium during the course of said reaction at least a finite concentration of from about 0.1 wt % up to less than 14 wt % of water together with (a) a salt soluble in the reaction medium at the reaction temperature in an amount operative to maintain a concentration of ionic iodide in the range of from about 2 to about 20 wt % effective as a catalyst stabilizer and co-promoter, (b) from about 1 to 20 wt % methyl iodide, (c) from about 0.5 to 30 wt % methyl acetate, (d) a partial pressure of hydrogen between about 0.1 and less than 3.5 psia at reaction conditions comprising 15 to 40 atmospheres total reaction pressure, and the concentration of hydrogen in the carbon monoxide fed to said carbonylation reactor is from about 0.001 mole percent to less than 0.25 mole percent (e) a rhodium concentration of at least 500 ppm by weight based on the weight of rhodium metal in the reaction mixture, and (f) acetic acid.

2. The improvement of claim 1 wherein said hydrogen is maintained at a partial pressure between about 1 and less than 3.5 psia.

3. The improvement of claim 1 wherein said hydrogen is maintained at a partial pressure between about 1.5 and less than 3.5 psia.

4. The improvement of claim 1 wherein said hydrogen partial pressure is maintained by venting or purging gaseous components of the reaction medium.

5. The improvement according to claim 1, wherein the concentration of hydrogen in the carbon monoxide fed to said carbonylation reactor is from about 0.005 mole percent to about 0.0250 mole percent.

6. The improvement according to claim 1, wherein the concentration of rhodium in the reaction medium is maintained between about 500 and 5000 parts per million rhodium by weight.

7. The improvement according to claim 6, wherein said rhodium concentration in said reaction medium is maintained in a range of from about 600 to about 2000 parts per million rhodium by weight.

8. The improvement according to claim 7, wherein said rhodium concentration in said reaction medium is maintained in a range of from about 750 to about 1500 parts per million by weight.

9. The improvement according to claim 1, wherein said salt is selected from the group consisting of quaternary ammonium salts, phosphonium salts, and salts of the Group IA and Group IIA metals.

10. The improvement according to claim 9, wherein said salt comprises lithium iodide or lithium acetate.

11. The process according to claim 9, wherein said salt comprises a quaternary ammonium iodide or acetate salt or a phosphonium iodide or acetate salt.

12. The process according to claim 9, wherein said salt comprises an iodide or acetate salt of sodium.

13. The process according to claim 9, wherein said salt comprises an iodide or acetate salt of potassium.

14. The improvement according to claim 1, wherein the concentration of water in the reactor is maintained at from about 1 wt % to about 10 wt %.

15. The improvement according to claim 14, wherein the partial pressure of hydrogen is maintained between about 1 and less than 3.5 psia.

16. The improvement according to claim 15, wherein the partial pressure of hydrogen is maintained between about 1.5 and less than 3.5 psia.

17. In a process for producing acetic acid by reacting methanol with carbon monoxide in a carbonylation reactor holding a reaction medium containing a catalytically effective amount of a rhodium, the improvement which comprises:

maintaining catalyst stability and system productivity by maintaining in said reaction medium during the course of said reaction from about 1 to about 10 wt % of water together with (a) a salt soluble in the reaction medium at the reaction temperature in an amount operative to maintain a concentration of ionic iodide in the range of from about 2 to about 20 wt % effective as a catalyst stabilizer and co-promoter, (c) from about 0.5 to 30 wt % methyl acetate, (d) a partial pressure of hydrogen between about 0.1 and less than 3.5 psi at reaction conditions comprising 15 to 40 atmospheres total reaction pressure, and the concentration of hydrogen in the carbon monoxide fed to said carbonylation reactor is from about 0.001 mole percent to less than 0.25 mole percent (e) a rhodium concentration of at least about 500 ppm rhodium by weight based on the weight of rhodium metal, and (f) acetic acid.

18. The improvement according to claim 17, wherein said rhodium concentration is maintained between about 750 ppm and 1500 ppm based on the weight of rhodium metal.

* * * * *